US009636093B2

(12) United States Patent
Longoria

(10) Patent No.: US 9,636,093 B2
(45) Date of Patent: *May 2, 2017

(54) METHODS OF TREATING A CARDIAC ARRHYTHMIA BY THORACOSCOPIC PRODUCTION OF A COX MAZE III LESION SET

(71) Applicant: LC Therapeutics, Inc., Sacramento, CA (US)

(72) Inventor: James Longoria, Sacramento, CA (US)

(73) Assignee: LC Therapeutics, Inc., Sacramento, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/069,436

(22) Filed: Mar. 14, 2016

(65) Prior Publication Data

US 2016/0192920 A1 Jul. 7, 2016

Related U.S. Application Data

(63) Continuation of application No. 14/087,701, filed on Nov. 22, 2013, now Pat. No. 9,308,040, which is a continuation of application No. 12/358,033, filed on Jan. 22, 2009, now Pat. No. 8,617,145.

(60) Provisional application No. 61/023,811, filed on Jan. 25, 2008.

(51) Int. Cl.
| | |
|---|---|
| A61B 18/02 | (2006.01) |
| A61B 18/04 | (2006.01) |
| A61B 18/12 | (2006.01) |
| A61B 18/18 | (2006.01) |
| A61B 18/20 | (2006.01) |
| A61B 17/00 | (2006.01) |
| A61B 18/14 | (2006.01) |
| A61B 18/24 | (2006.01) |
| A61N 7/02 | (2006.01) |
| A61B 18/08 | (2006.01) |
| A61B 18/00 | (2006.01) |

(52) U.S. Cl.
CPC ........ *A61B 17/00234* (2013.01); *A61B 18/02* (2013.01); *A61B 18/04* (2013.01); *A61B 18/082* (2013.01); *A61B 18/12* (2013.01); *A61B 18/1482* (2013.01); *A61B 18/1492* (2013.01); *A61B 18/18* (2013.01); *A61B 18/1815* (2013.01); *A61B 18/20* (2013.01); *A61B 18/24* (2013.01); *A61N 7/022* (2013.01); *A61B 18/1445* (2013.01); *A61B 2017/00243* (2013.01); *A61B 2018/00375* (2013.01); *A61B 2018/00577* (2013.01); *A61B 2018/1861* (2013.01)

(58) Field of Classification Search
CPC ...... A61B 18/1492; A61B 2017/00243; A61B 2018/00577; A61B 18/02; A61B 18/18; A61B 2017/00106; A61B 18/24; A61B 2018/00029; A61B 2017/00247; A61B 2018/00392; A61B 2018/0212; A61B 18/1815

See application file for complete search history.

(56) References Cited

U.S. PATENT DOCUMENTS

| | | | |
|---|---|---|---|
| 6,010,531 A | 1/2000 | Donlon et al. | |
| 6,012,457 A | 1/2000 | Lesh | |
| 6,090,084 A | 7/2000 | Hassett et al. | |
| 6,325,797 B1 | 12/2001 | Stewart et al. | |
| 6,652,518 B2 | 11/2003 | Wellman et al. | |
| 6,849,075 B2 | 2/2005 | Bertolero et al. | |
| 7,207,988 B2 | 4/2007 | Leckrone et al. | |
| 7,264,587 B2 | 9/2007 | Chin | |
| 7,387,126 B2 | 6/2008 | Cox et al. | |
| 8,617,145 B2 * | 12/2013 | Longoria | A61B 18/02 128/898 |
| 9,308,040 B2 * | 4/2016 | Longoria | A61B 18/02 |
| 2004/0102804 A1 | 5/2004 | Chin | |
| 2005/0182298 A1 | 8/2005 | Ikeda et al. | |
| 2006/0270900 A1 | 11/2006 | Chin et al. | |
| 2006/0271032 A1 | 11/2006 | Chin et al. | |
| 2007/0083193 A1 | 4/2007 | Werneth et al. | |
| 2007/0185479 A1 | 8/2007 | Lau | |
| 2008/0065061 A1 | 3/2008 | Viswanathan | |

OTHER PUBLICATIONS

Cox, The role of surgical intervention in the management of AF. Texas Heart Institute Journal 2004;31(3):257-65.
Edgerton et al., Minimally invasive Pulmonary Vein Isolation and Partial Autonomic Denervation for Surgical Treatment of Atrial Fibrillation. Ann Thorac Surg 2008;86:35-9.
Essebag et al., Non-inducibility post-pulminary vein isolation achieving exit block predicts freedom from atrial Fibrillation. European Heart Journal, Advanced Access Sep. 23, 2005; 6 pages.
Gillinov, Choice of Surgical Lesion Set: Answers From the Data Ann Thorac Surg 2007; 84: 1786-92.
Longoria et al., Totally Thoracoscopic Surgical Ablation for Atrial Fibrillation. ArtiCure Exhibitor Booth, 87th Annual Meeting, American Association for Thoracic Surgery, Washington DC (2007) May 5, 2007; 46pp.
Longoria et al., Totally thoracoscopic bipolar radiofrequency ablation for the treatment of atrial fibrillation. Presentation for Society of Thoractic Surgery, 2009.
McClelland, Preliminary results of a limited throacotomy: new approach to treat atrial fibrillation. J Cardiovasc Electrophysiol 2007:1-7; Abstract.
Mehall et al., Intraoperative epicardial electrophysiologic mapping and isolation of autonomic ganglionic plexi. Ann. Thorac. surg. 2007;83:1724-30.
Nademanee, A new approach for catheter ablation of atrial fibrillation: mapping of the electrophysiologic substrate. J. Am. Coll. Cardiol. 2004;43:2044-53.
Sagbas et al., "Video-assisted bilateral epicardial pulmonary vein isolation for the treatment of lone Atrial Fibrillation", The Annals of Thoracic Surgery, 2007; 83: 1724-1730; Published May 2007.

(Continued)

Primary Examiner — Audrea Buckley
(74) Attorney, Agent, or Firm — Bret E. Field; Bozicevic, Field & Francis LLP

(57) ABSTRACT

Methods of treating a subject for a cardiac arrhythmia are provided. Aspects of the methods include thoracoscopically producing a cardiac Cox maze III set of lesions in cardiac tissue of the subject in a manner sufficient to treat the subject for the cardiac arrhythmia.

20 Claims, 4 Drawing Sheets

(56) References Cited

OTHER PUBLICATIONS

Salenger et al., the completely endoscopic treatment of AF: Report on the first 14 patients with early results. The Heart Surgery Forum 2004;7(6):E555-8.
Saltman, A completely endoscopic approach to microwave ablation for AF. The Heart Surgery Forum 2003;6(3): E38-41.
Sirak et al., Toward a definitive, totally thoracoscopic procedure for atrial fibrillation, Ann. Thorac. Surg. 2008;86:1960-4.
Van Boven et al., Surgical treatment of Af denervation of ganglionic plexi. Lecture Nov. 1-2, 2007.
Yilmaz et al., Completely thorascopic bilateral pulmonary vein isolation and left atrial appendage exclusion for AF. J. Thorac. Cardiovasc. Surg. 2008;136:521-22.

\* cited by examiner

METHODS OF TREATING A CARDIAC ARRHYTHMIA BY THORACOSCOPIC PRODUCTION OF A COX MAZE III LESION SET

This application is a continuation of U.S. patent application Ser. No. 14/087,701 filed Nov. 22, 2013, which is a continuation of U.S. patent application Ser. No. 12/358,033 filed Jan. 22, 2009, now U.S. Pat. No. 8,617,145, which, pursuant to 35 U.S.C. §119 (e), claims priority to the filing date of the U.S. Provisional Patent Application Ser. No. 61/023,811 filed Jan. 25, 2008; the disclosure of which applications are herein incorporated by reference.

INTRODUCTION

Atrial fibrillation (AF) is the most common form of cardiac arrhythmia leading to hospital admission. Over 2.2 million Americans are affected by AF and approximately 160,000 new cases are identified annually. In addition, the risk for atrial fibrillation increases with aging. It is estimated that subjects over 80 years of age have a 10% chance of having atrial fibrillation. The ideal of treating large numbers of patients with isolated AF has remained elusive due to the invasiveness of the Cox maze III operation, which is considered to be the gold standard for surgical therapy of atrial fibrillation.

The past several years have seen the development of a number of procedures that have attempted to treat AF with a less invasive approach. Ablative therapies for AF, including both catheter and surgical therapies, have undergone a significant change by devising lesion sets modeled after the Maze operation. Nonicisional ablative modalities have also proliferated and include cryoablation, microwave, radiofrequency, laser, and high-intensity focused ultrasound. However, none of these approaches are able to provide a complete Cox maze III set of lesions through a thoracoscopic approach.

SUMMARY

Methods of treating a subject for a cardiac arrhythmia are provided. Aspects of the methods include thoracoscopically producing a cardiac Cox maze III set of lesions in cardiac tissue of the subject in a manner sufficient to treat the subject for the cardiac arrhythmia.

DETAILED DESCRIPTION

Figure 1:
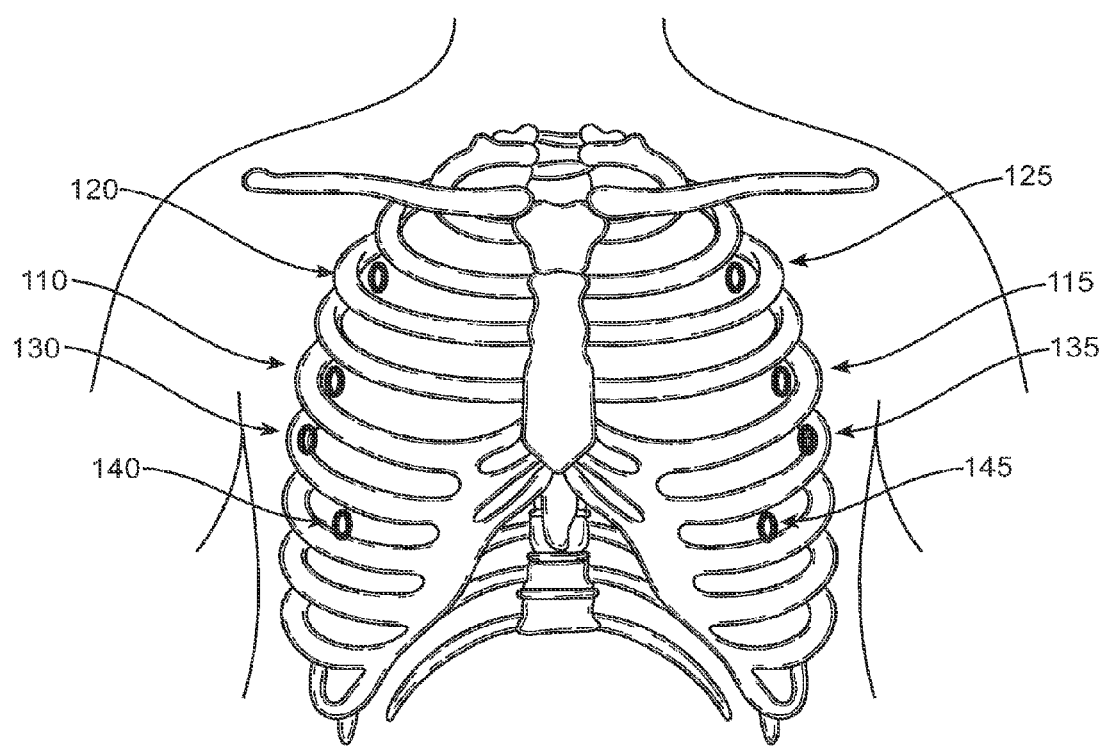
FIG. 1 provides a schematic view of the chest, demonstrating an embodiment of the access ports used to perform the methods of the invention.

Methods of treating a subject for a cardiac arrhythmia are provided. Aspects of the methods include thoracoscopically producing a cardiac Cox maze III set of lesions in cardiac tissue of the subject in a manner sufficient to treat the subject for the cardiac arrhythmia.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the methods include thoracoscopically producing a Cox maze III set of lesions in a subject. By "thoracoscopically producing" or "thoracoscopically" is meant methods which are performed through one or more thoracoscopic body openings using a thoracoscope or a thoracoscopic instrument for procedures such as visualization, surgery, the conduction of diagnostic tests, etc., in or adjacent to the thoracic cavity. Similarly, a "thoracoscopic procedure" is a procedure in which visualization, surgery, a diagnostic test, etc., is performed by gaining access to the chest through one or more thoracoscopic body openings using a thoracoscope, or a thoracoscopic instrument.

By "thoracoscope" or "thoracoscopic instrument" is meant a thin tube-like instrument used to examine or enter the inside of the thoracic cavity of a subject, e.g., the pleural space of a subject. A thoracoscope is a type of endoscope, which is a general term for a thin tube-like instrument for examining the inside of the body. A thoracoscope can have a light and a lens or camera for viewing the inside of the chest, and can also have one or more tools that can be used with a thoracoscope, such as a sewing device, a cutting device, an ablation device, a grasping device, a retracting device, etc. In some embodiments, a single thoracoscopic instrument can have more than one function (e.g., camera and cutting functions, or light and sewing functions, etc.) In addition, although the methods discussed below disclose the use of a particular number of thoracoscopic instruments, the methods of the invention can include using any suitable number of thoracoscopic instruments, such as one or more, two or more, three or more, four or more, etc. In addition, the methods can include use of the thoracoscopic instruments sequentially, or simultaneously, including simultaneous use of bilateral thoracoscopic instruments.

Access to the thoracic cavity can be achieved by percutaneously creating a opening into the chest cavity through a skin incision in the intercostal space (ICS) between two adjacent ribs, and inserting an instrument such as a trocar, cannula, thoracoscope, thoracoscopic instrument or the like through the opening. One or more openings, or "ports" can be created in one or more locations in the intercostal spaces of the chest, depending on the procedure to be performed and the thoracoscopic instruments to be used. One or more thoracoscopes or thoracoscopic instruments can be advanced through at least one of the openings, or thoracoscopic body openings. The creation of additional openings can allow for the use of accessory instruments. In some embodiments, a pneumothorax is created during the thoracoscopic procedure, i.e., $CO_2$ is introduced into the pleural space which surrounds the lung, to collapse the lung and improve the view of the surgical field.

The methods of the subject invention are minimally-invasive methods, such that the thoracoscopic body openings created in the subject's body are small, for example, 3 centimeters or less in greatest dimension, 2 centimeters or less in greatest dimension, 12 millimeters or less in greatest dimension, or 5 millimeters or less in greatest dimension. In some embodiments, all of the thoracoscopic body openings created in the subject's body measure no more than 12 millimeters in greatest dimension. In some embodiments, therefore, "thoracoscopically producing" includes making a thoracoscopic body opening that measures no more than 12 mm in greatest dimension. In some embodiments, "thoracoscopically producing" includes making all of the thoracoscopic body openings no more than 12 millimeters in greatest dimension. This is in contrast to a "mini-thoracotomy" in which an incision which can measure 5 centimeters or 8 centimeters or more is utilized for gaining access to the thoracic cavity. The thoracoscopic methods can allow access to the epicardial surface of the heart.

In some embodiments, the thoracoscopic body openings or ports are produced bilaterally, i.e., on both sides of the subject's body. In some embodiments, the number of thoracoscopic body openings or ports may range from 2 to 6 ports on each side, such as from 3 to 5 ports, or 4 ports on each side. The number of ports produced can vary depending on the subject, the procedure to be performed, the lesions to be created, and the thoracoscopic instruments to be used.

In one embodiment, the thoracoscopic body openings that are created on the right side of a subject include an opening in the $2^{nd}$ or $3^{rd}$ ICS, 1 to 2 centimeters medial to the anterior axillary line; an opening in the $4^{th}$ ICS 1 to 2 centimeters posterior to the anterior axillary line; an opening in the $5^{th}$ ICS in the mid-axillary line; and an opening in the $6^{th}$ ICS in the anterior axillary line. In some embodiments, the thoracoscopic body openings that are created on the left side of a subject include an opening in the $2^{nd}$ ICS 1 to 2 cm medial to anterior axillary line; an opening in the $3^{rd}$ or $4^{th}$ ICS 1 to 2 centimeters posterior to the anterior axillary line; an opening in the $5^{th}$ ICS in the mid-axillary line; and an opening in the $6^{th}$ ICS in the anterior axillary line. In some embodiments, at least one of the thoracoscopic body openings is an opening in the $2^{nd}$ ICS on either the right or left side. In other embodiments, at least one of the thoracoscopic body openings is an opening in the $3^{rd}$ ICS, located medial, or anterior to the anterior axillary line on either the right or left side. Although the above combination of ICS openings can be used in some embodiments of the invention, the methods can include placement of thoracoscopic body openings which can vary in location, for example, an opening in the $6^{th}$ ICS can be 1 centimeter posterior to the anterior axillary line, or more than one opening can be made in the same ICS.

As discussed above, the Cox maze III procedure is a type of heart surgery for treatment of atrial fibrillation. The surgery as described is done via a median sternotomy (vertical incision through the breastbone), and cardiopulmonary bypass (stopping the heart and circulating the blood outside of the body) in order to create a "maze", or an extensive series of incisions that are made in the wall of the atria in a maze-like pattern. The incisions which are subsequently sutured back together result in areas of scar in the cardiac tissue which can block the abnormal electrical circuits that are seen in AF. The goal of the procedure is therefore to eliminate atrial fibrillation and have the patient return to a normal sinus rhythm as a result of the scarring in the region of the incisions.

In the methods of the subject invention, a Cox maze III set of lesions is be thoracoscopically produced, i.e., without the need for a median sternotomy, or even a mini-thoracotomy (e.g., a chest incision of 5 centimeters). In methods of the invention, a "lesion" or "scar" can be created by ablating cardiac tissue from the epicardial surface of the heart, which is in contrast to methods of creating the lesions from the endocardial surface, or inside surface, of the heart as with an open surgery or a catheter procedure. By "lesion" or "ablation line" is meant an area of cardiac tissue that has been ablated. By "ablation" is meant a process of removing or altering the electrically-conducting tissue in an area of interest, such that the tissue no longer conducts or generates an electrical impulse sufficient to generate or propagate an arrhythmia. The process of ablation can prevent an arrhythmia from developing because the cardiac tissue which provides a trigger for an arrhythmia has been destroyed. The process of ablation can also prevent an arrhythmia from propagating to other areas of the heart by the creation of a line, or lesion, which electrically isolates the tissue and blocks passage of the electrical impulse. Ablation can be performed with a variety of types of energy, such as radiofrequency energy, laser energy, microwave energy, cryothermy, and the like. Ablation "lines" or "lesions" can be focal areas which are separate from other areas of ablation, or they can be contiguous, such they form lines or lesions connected to each other, which can form, for example, a continuous line, or ring, or circle, in order to electrically isolate an area of cardiac tissue.

Figure 4:
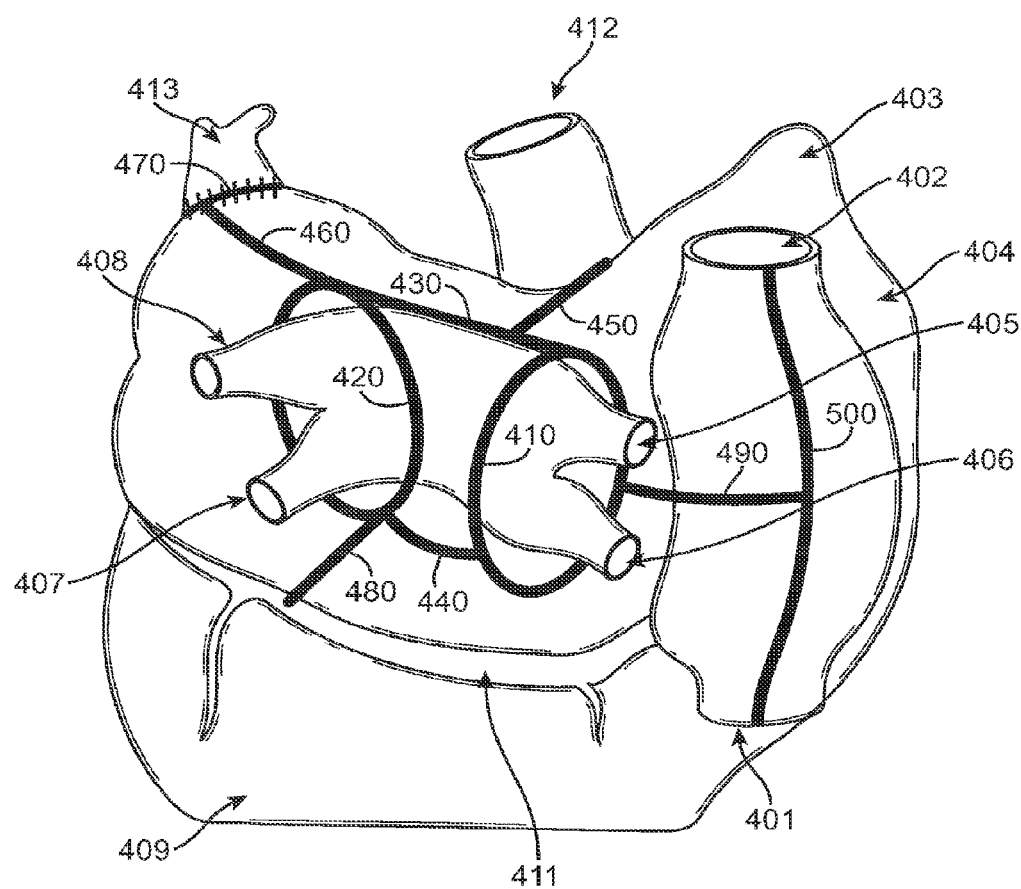
FIG. 4 provides a schematic view of the heart, demonstrating a map of the ablation lesions that can be created using the methods of the subject invention.

By "Cox maze III" set of lesions is meant a group of lesions chosen from among the following ablation lines: a right pulmonary vein encircling ablation line 410 as shown in FIG. 4, a left pulmonary vein encircling ablation line 420, a superior connecting ablation line connecting the right and left pulmonary vein encircling lines 430, an inferior connecting ablation line connecting the right and left pulmonary vein encircling lines 440, an ablation line connecting the superior ablation line to the fibrous trigone 450, an ablation line connecting the superior ablation line to the base of the left atrial appendage 460, and an ablation line extending from the inferior connecting ablation line to the coronary sinus 480. The combination of ablation lines 410, 420, 430, and 440 comprises what is known as the "box lesion" set. As such, in some instances, the Cox maze III lesion set produced by methods of the invention is a box lesion set.

In some embodiments, the set of lesions making up the Cox Maze III lesion set according to the methods of the subject invention further includes one or more additional lesions in addition to the box lesion set. In some instances, Cox Maze III lesion sets of the invention may include amputation of the left atrial appendage, or a left atrial appendectomy (element 470). In some embodiments, the set of lesions produced by methods of the invention further includes an ablation line in the posterolateral wall of the right atrium connecting the superior vena cava to the inferior vena cava, shown as element 500 in FIG. 4. In some embodiments, the set of lesions also includes an ablation line connecting the right pulmonary vein encircling ablation line to an ablation line in the posterolateral wall of the right atrium connecting the superior vena cava to the inferior vena cava, shown as element 490 in FIG. 4. In some embodiments, the methods of the subject invention further include ablation of autonomic ganglionic plexi on the epicardial surface of the atrium. In some embodiments, the methods of the subject invention can include ablation of complex fractionated atrial electrograms, discussed further below.

In some instances, the methods include first identifying a subject in need of surgical treatment for a cardiac arrhythmia. A subject who needs surgical treatment for an arrhythmia can include, for example, subjects who are symptomatic, subjects who are asymptomatic but cannot be adequately anticoagulated to reduce their risk of stroke, subjects who have failed medical therapy, subjects who have failed catheter ablation, subjects who cannot tolerate the side effects of anti-arrhythmic drugs, or subjects who choose surgical ablation as a preferred method.

A patient in need of surgical treatment for a cardiac arrhythmia can be prepared for surgery in the conventional manner. General anesthesia, when desired, can be provided using any convenient protocol, e.g., via administration of an anesthetic agent with a double-lumen endotracheal tube in order to provide single lung ventilation. In some embodiments, transesophageal echocardiography monitoring is performed during the entire procedure.

The methods of the subject invention can be performed on a beating heart, i.e., without cardiopulmonary bypass, and the methods can also be performed in a patient on cardiopulmonary bypass, i.e., a stopped heart. The procedure may be performed on the right side first, followed by the left side as outlined below, or alternatively, the procedure may be performed on the left side first, followed by the right side.

For a right thoracoscopic approach, the operating table can be tilted slightly to the left side with a slight tilt, such as a 15 degree tilt. After the right lung is deflated, one or more ports, or openings, can be created in the right side of the chest, as disclosed above. In one embodiment, as shown in FIG. 1, four ports can be utilized for performing the methods of the subject invention. In FIG. 1, a first port is placed in the $4^{th}$ intercostal space (ICS) 1 centimeter posterior to the anterior axillary line, shown as element 110. A thoracoscope can then be introduced and the right hemithorax visually inspected. Humidified $CO_2$ can be introduced into the thoracic cavity at a pressure sufficient to allow adequate visualization for the methods of the invention (e.g., 8 mm Hg pressure). This pressure can be maintained throughout the procedure. A second port can be placed in the $2^{nd}$ or $3^{rd}$ ICS 1 to 2 cm medial to anterior axillary line, shown as element 120 in FIG. 1. The placement of this most cephalad port, in the $2^{nd}$ or $3^{rd}$ ICS 1 to 2 cm medial to anterior axillary line, allows for the creation of a lesion in the region of the aorto-mitral confluence, or anterior fibrous trigone. A third port can be placed in the $5^{th}$ ICS mid-axillary line, shown as element 130 in FIG. 1. A fourth port, element 140 in FIG. 1, can be placed in the $6^{th}$ ICS in the anterior axillary line.

A second grasping forceps can then be introduced through any of the three other ports. A first opening is created in the pericardium, which is the fibrous sac surrounding the heart, to allow access to the epicardial surface of the heart. In some embodiments, the pericardium is opened cephalad to, or just above, the confluence of the right atrial appendage and ascending aorta. The pericardial opening can be located approximately 1 to 2 cm anterior and parallel to the right phrenic nerve. This opening can be extended cephalad, or in a superior direction, e.g., to the level of the aorta, and can then be extended inferiorly, e.g., to the level of the inferior vena cava (IVC), or to the level of the diaphragm.

One or more traction sutures can be placed in the pericardial tissue, in order to retract the edges of the pericardium away from the pulmonary veins. These traction sutures can be placed utilizing an Endo Stitch™ (Autosuture™, Covidien, Mansfield, Mass.), for example, or other similar suture device designed to be used with a thoracoscope. The ends of the one or more traction sutures are exteriorized, or brought outside one of the port incisions, and secured.

Both the oblique sinus (element 201 in FIG. 2) and transverse sinus (element 202 in FIG. 2) can then be opened using both sharp and blunt dissection techniques. The oblique sinus can be opened bluntly by using one or more endoscopic soft tissue dissectors (for example, using an endoscopic Kittner, which is a Dacron™ coated soft tip tissue dissector, or any other soft tissue dissector suitable for use with an endoscopic or thoracoscopic instrument). The oblique sinus is one of two pericardial sinuses (oblique and transverse) which are pouches or cul-de-sacs of the pericardium located behind the heart. The oblique sinus is located behind the left atrium, between the right and left pulmonary veins. The right thoracoscopic approach to the oblique sinus is shown as element 250 in FIG. 2, which is a schematic view of the posterior wall of heart as viewed from the front, with the remainder of the heart removed for clarity. Additional anatomic landmarks shown in FIG. 2 include the superior 205 and inferior 206 venae cavae, ascending aorta 207, pulmonary artery 208, and diaphragm 209.

The transverse sinus 202 can then be entered by retracting the SVC anteriorly, and entering between the superior vena cava above and the pulmonary veins below. The retraction of the SVC can be facilitated by using a soft tissue dissector as described above, which has been inserted through one of the superior ports, e.g., a port in the $2^{nd}$ or $3^{rd}$ ICS. Entry into the transverse sinus is confirmed with visualization of the left atrial appendage. The right thoracoscopic approach to the transverse sinus is shown as element 260 in FIG. 2. An articulating or hinged dissector with a firm tip, such as the Wolf™ Lumitip™ dissector (Atricure, Inc., Cincinnati, Ohio) can be introduced through the oblique sinus and then maneuvered behind the heart until the tip exits the transverse sinus posterior to the right set of pulmonary veins. Any other suitable dissector may be used with the subject methods such as a curved Satinsky clamp, for example. In some embodiments, the dissector can have a light on the tip of the dissector. After the dissector reaches the transverse sinus, the posterior space between the pericardium and left atrium can be enlarged with blunt dissection. The dissector is then removed.

In some embodiments, a combination ablation and sensing device such as the Isolator® Multifunctional Pen (Atricure, Inc., Cincinnati, Ohio) can be introduced into the thoracic cavity via any of the three ports. The sensing portion of the device can be used to sense the pulmonary veins, to create a baseline map of the right pulmonary vein potentials. Additionally, in some embodiments, the methods can also include sensing in order to localize the ganglionic plexi. Autonomic ganglionic plexi (GP) are collections of nerves located on the surface of the heart. Autonomic GP can promote pulmonary vein arrhythmogenicity and facilitate induction of sustained atrial fibrillation by premature atrial depolarizations. The autonomic GP can therefore function as regulators of both pulmonary vein- and non-pulmonary vein-dependent mechanisms of atrial fibrillation. The GP can be mapped with high-frequency stimulation (e.g., at a rate of 800-1,000 impulses per minute), at a voltage (e.g., 18 volts) using any suitable sensing device. When the GP are stimulated they release acetylcholine, a neurotransmitter which is a potent blocker of the atrioventricular node (AV) node, the area of specialized tissue between the atria and the ventricles of the heart which conducts the normal electrical impulse from the atria to the ventricles. Acetylcholine can also slow down the sinoatrial node (SA node or sinus node) as well, which is the impulse-generating (pacemaker) tissue located in the right atrium of the heart, and thus the generator of sinus rhythm.

Release of acetylcholine by a stimulated GP can result in a significant decrease in heart rate (a bradycardic response). If a significant bradycardic response is seen (e.g., an increase in R-R of 50% or greater) after stimulation of a GP, this confirms the presence of an active GP which can be focally ablated. If there is no response when an area of tissue is stimulated (e.g., no significant increase in the R-R interval during stimulation) the stimulating device can be moved, and another area can be tested.

In some instances, a stimulating device, such as the pen disclosed above, can be placed in a location where a ganglionic plexus is known to be located, and then the ablating agent can be activated (e.g., radiofrequency energy), and the ganglionic plexus can be focally ablated. One or more ganglionic plexi can be ablated from the epicardial approach, using the devices as disclosed above. The methods can include repeating the ablating steps if necessary one or more times until it is determined that the GP has been ablated (e.g. no significant increase in the R-R interval is seen during stimulation). Further details of techniques of GP mapping and ablation that can be adapted for use with the subject methods are disclosed, for example, in the publication by Mehall, et al., entitled "Intraoperative Epicardial Electrophysiologic Mapping and Isolation of Autonomic Ganglionic Plexi". Therefore, in some embodiments, the methods can include thoracoscopically producing a lesion in a ganglionic plexus. After this step, the above sensing steps can be repeated to confirm conduction block post-ablation, discussed further below. The evaluation of ablation can be performed with the Isolator® Multifunctional Pen, or any other device suitable for thoracoscopic procedures that performs a similar function. The stimulating and sensing device can then be removed.

As discussed above, by "ablation" is meant a process of removing or altering the electrically-conducting tissue in an area of interest (e.g., a GP) such that the tissue no longer conducts or generates an electrical impulse sufficient to generate or propagate an arrhythmia. In some embodiments, ablation can be performed by directly contacting a portion of cardiac tissue with an ablation device, in a manner sufficient to create a lesion. In other embodiments, ablation can be performed by delivery of an ablating agent to cardiac tissue. For example, in some embodiments, an ablation device can be located sufficiently close to an area of cardiac tissue of interest, such that an ablating agent, (e.g., laser energy) is delivered to the cardiac tissue in a manner sufficient to create a lesion. The form of energy used for ablating cardiac tissue can be radiofrequency or cryoablation energy, for example. In some embodiments the ablation is transmural, i.e., extends through the entire heart wall. In other embodiments, the ablation does not extend through the entire thickness of the cardiac wall; however, the degree of ablation may be sufficient to block electrical conduction. Any suitable device can be used for ablation, such as the Isolator® Multifunctional Pen disclosed above, or other similar device such as the Cardioblate™ Ablation System (Medtronic, Minneapolis, Minn.), the AFx FLEX 10™ microwave ablation probe (Guidant corporation), the Surgifrost™ Cryoablation System (Cryocath Technologies), or the Epicor™ High Intensity Focused Ultrasound Cardiac Ablation system (St Jude Medical, St Paul, Minn.), for example.

The methods of ablation can include contacting a portion of cardiac tissue with an ablation device to form a lesion. The methods can further include repeating the contacting and ablating steps a number of times to produce a plurality of lesions. For example, the contacting step may be performed two or more times, such as three or more, or four or more times, etc. In some embodiments, the contacting and ablating step is performed in the same location. In some embodiments, the contacting and ablating step can be performed in overlapping locations, such that part of a second location overlaps with part of a first ablating location, such as in the case of creating a continuous linear ablation line. In other embodiments, a second ablation step may be in a different location from the first ablation step, as in the ablation of a ganglionic plexus or a complex fractionated atrial electrogram, discussed further below. Although the methods of ablation as described use contact of cardiac tissue in order to achieve ablation, in some embodiments ablation can be achieved by using an ablation device in proximity to cardiac tissue, for example, in delivering an ablation agent to the cardiac tissue.

The devices that can be used with embodiments of the invention are devices that are configured to ablate, or remove, or sufficiently alter electrically-conducting cardiac tissue. In some embodiments, the ablation is achieved by using a form of energy, such as radiofrequency or cryoablation energy. The subject devices are devices that can be used in endovascular, minimally invasive surgical, open surgical, or other interventional procedures. Any suitable device can be used for ablation, such as the ablation devices disclosed above, or other similar devices such as those devices in the Cardioblate™ Ablation System (Medtronic, Minneapolis, Minn.), the AFx FLEX 10™ microwave ablation probe (Guidant corporation), the SurgiFrost®/FrostByte™ Cryoablation System (Cryocath Technologies), or the Epicor™ High Intensity Focused Ultrasound Cardiac Ablation system (St Jude Medical, St Paul, Minn.), for example.

An ablation device of the subject methods can be in the shape of a clamp, with an upper and a lower jaw, such that the ablation device is a clamping device. In other embodiments, the ablation device can have an elongated cylindrical shape, such as that of a pen. In some embodiments, the ablation device can have a linear shape, a rectangular shape, a semi-circular shape, an "L" shape, a "U" shape, or any other suitable shape. The configuration of the surface of the ablation device that contacts the tissue can also be any suitable two-dimensional shape such as a line, a square, an oval, a triangle, etc. In some embodiments, the ablation device can further employ suction to pull tissue into the device.

The area of cardiac tissue that is ablated will depend on the type of ablation device (e.g., clamp, or pen) and the shape of the portion of the ablation device that contacts the tissue (e.g., rectangular area; circular area). The total area of cardiac tissue that is ablated will further depend on the type and strength of the energy used (e.g., radiofrequency (RF) energy, high intensity focused ultrasound energy) and the length of time that the device is in contact with tissue, for example.

For example, an elongated cylindrical device may have a circular area at one end of the device that of contacts cardiac tissue, and after application of the ablating energy may form an area of ablated tissue that approximates a cone-shaped area of tissue, extending to a particular depth, such as 6 mm, for example. In the case of an ablation device in the shape of a clamp, the area of the ablated tissue between the jaws of the clamp can be a rectangular area, with the approximate dimensions of the clamp. For example, if the jaws of the clamp are each 4 cm long and 5 mm wide, the ablated area can be a rectangular area 4 cm in length and 5 mm in width, with a depth equal to the area of tissue between the jaws of the clamp. In some embodiments, the area of ablated tissue may be greater than the area which was in direct contact with the ablation device, such as 10% greater or more, or 20% greater or more, etc. Furthermore, the shape of the ablated area once ablation has been completed can be any suitable three-dimensional shape such as a cylinder, cone, pyramid, cube, sphere, etc.

The ablation device can include, but is not limited to devices that use radiofrequency (RF) energy, including bipolar radiofrequency energy or bipolar irrigated RF energy, cryoablation, laser energy, microwave energy, thermal energy, a thermo-electric chip device, ultrasound energy, including high intensity focused ultrasound energy, an ablating drug delivery device, and any combinations thereof. For example, the ablation device can be a bipolar radiofrequency (RF) device such as the Isolator® Synergy™ Cardiac Ablation Clamp (Atricure, Inc., Cincinnati, Ohio). This system consists of a power generator, bipolar clamp, and a pacing, sensing, stimulator, bipolar RF pen. The device delivers RF energy with resultant heating of the tissue and can complete a transmural lesion. The term bipolar indicates that the ablation path extends locally between two electrodes in the device, rather than between one electrode and a general remote, or external electrode. Although the current methods can be used with this system, the technique is equally applicable to other types of ablation devices. For example, in some embodiments, the ablation device can be a laser energy device, a microwave energy device, a thermal energy device, an ultrasound device, a cryoablation device, etc. In some embodiments, the methods can include other methods of ablation, such as surgical incision.

The process of ablation can be performed by direct contact of the ablation device with cardiac tissue, and in some embodiments ablation can be performed with delivery of an ablation agent in sufficient proximity to the cardiac tissue of interest. The process of ablation is continued until sufficient conduction block is achieved in the desired area. This can require 1 to 4 or more applications of the device or agent, such as two applications or more, or three applications or more, etc. In addition, the process of ablation can be monitored as the ablation is performed. In some embodiments, the process of ablation can be guided by a feedback parameter, such as impedance, temperature, conductivity, etc. For example, if radiofrequency energy is used, the impedance of the tissue can be monitored and the power output of the device can be designed so that it is inversely proportional to the impedance of the tissue, such that overheating of the tissue does not occur. In some embodiments, the process of ablation can be continued for a specific period of time, which can be determined by the thickness or composition of the tissue to be ablated, or the anatomical location of the tissue to be ablated, for example.

The subject methods may also include intraoperative electrophysiologic testing of the cardiac tissue to confirm the presence of a lesion. This step can be used to detemine whether or not a first ablating step produced sufficient removal or alteration of the electrical conduction of the tissue in order to block electrical conduction. If it is determined that sufficient ablation has not been achieved, the contacting and ablating steps can be repeated until sufficient conduction block is confirmed. Intraoperative testing for conduction block can include sensing for electrical signals on either side of an ablation line, for example, to verify that the ablation line is complete (e.g., transmural) and continuous, and that electrical impulses are not crossing the ablation line. Testing for conduction block can also include sensing for electrical signals on the ablation line that has been created. In some embodiments, a sensing pen, such as a bipolar radiofrequency pen, can be placed on the ablation line itself, and the strength of the sensed electrical signals can be determined. For example, it may be determined that a sensor placed on an ablation line may demonstrate a reduction in amplitude of the EKG, such as an 80%, or 90% reduction in amplitude of the EKG, which can be an indication of the degree of ablation. Intraoperative electrophysiologic testing can be performed, for example, by measuring the change in conductive properties of the tissue as it is being ablated. In some embodiments, intraoperative testing for can include testing for uni- or bi-directional block. The presence of uni- or bi-directional block can be confirmed with a sensing device, such as the combination ablation and sensing device disclosed above. For example, cardiac tissue can be tested for "entrance" block, meaning that an electrical signal or impulse cannot pass from the atrial side of a lesion to the pulmonary veins. If a subject is in sinus rhythm, the tissue can also be tested for "exit" block, meaning that an electrical signal or impulse cannot pass from the pulmonary veins to the atrial tissue on the other side of an ablation line. If both "entrance" and "exit" block is present, then bidirectional block can be confirmed. If the subject is not in sinus rhythm (e.g., atrial fibrillation), only unidirectional "entrance" block can be confirmed, as it is not possible to evaluate whether or not an electrical signal has traveled from the pulmonary veins to the atrial tissue in the presence of atrial fibrillation.

After the ganglionic plexi have been mapped and ablated, a soft tissue dissector can then be re-introduced through the anterior, or cephalad port incision (element 120 in FIG. 1) with a flexible guiding element, such as the Glidepath™ Transfer Tape (Atricure, Inc., Cincinnati, Ohio), or a red rubber catheter, such as a 14 French catheter, or similar device, attached. The flexible guiding catheter or tape can then be placed through the transverse sinus 202 with the tip posterior to the right set of pulmonary veins. The dissector with the attached guiding catheter or tape can be maneuvered until the tip exits through the oblique sinus 201 between the right inferior pulmonary vein and the IVC. The guiding catheter or tape can be grasped and pulled outside of the chest, and the dissector disarticulated and removed. The guiding catheter or tape now forms a path between the transverse sinus and the oblique sinus, shown as element 270 in FIG. 2. Alternatively, the guiding catheter can be placed from the oblique sinus to the transverse sinus. The distal end of the Glidepath catheter can be attached to an ablation device, such as an Isolator® Synergy™ Cardiac Ablation Clamp (Atricure, Inc., Cincinnati, Ohio) or other similar device, as disclosed above.

Figure 3:
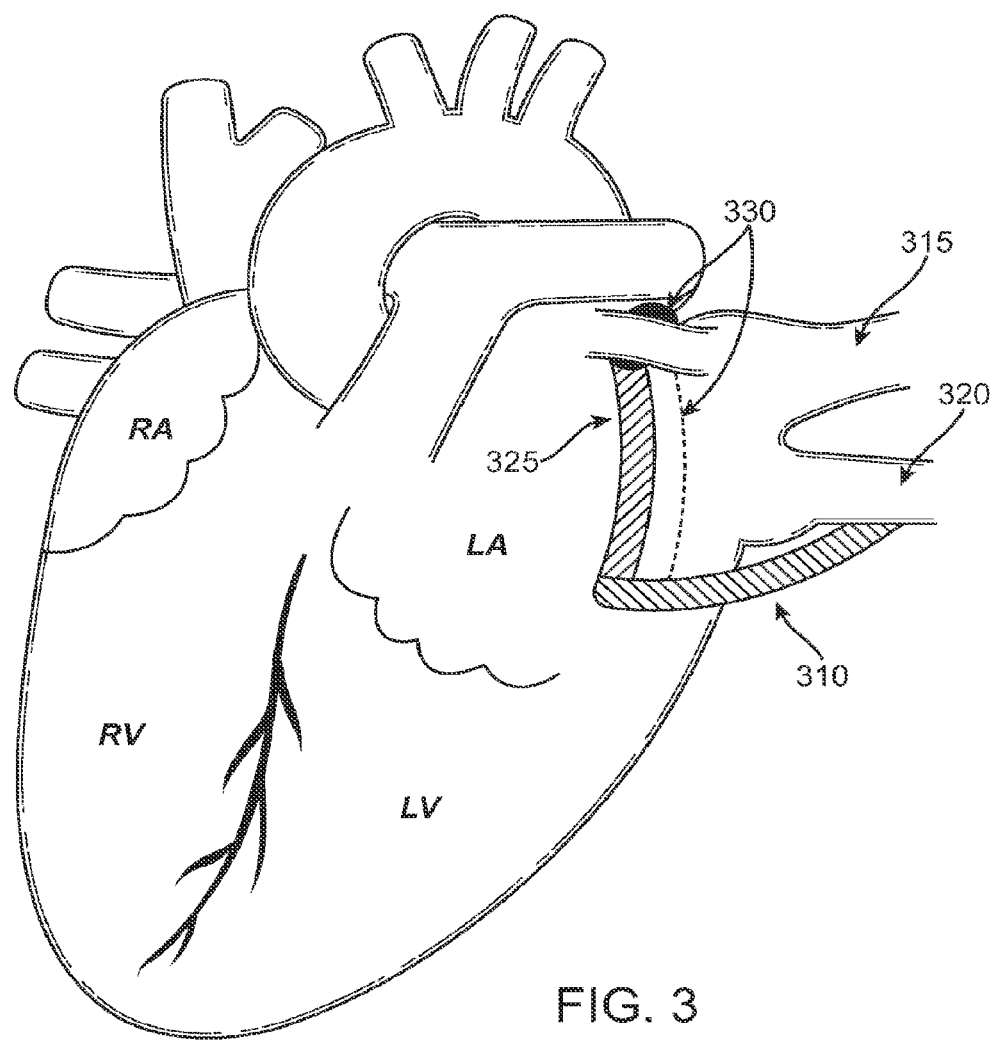
FIG. 3 provides a schematic view of the heart, demonstrating an embodiment of the clamping method which can be used according to methods of the invention.

Once the distal end of the Glidepath catheter is attached to an ablation device, the ablation device can be introduced into the right hemithorax and the guiding catheter tape is used to guide one jaw of the clamp behind the right pulmonary veins while the other jaw is passed in front of the veins, as shown in the front view of the heart as in FIG. 3. In this view, the left atrium is indicated as LA, the right atrium is indicated by RA, the left ventricle by LV, and the right ventricle by RV. Clamping of the left pulmonary veins is shown for illustration in FIG. 3. Clamping of the right pulmonary veins, although not shown, can be performed in a similar manner. In some embodiments, while clamping the right pulmonary veins, some or all of the inter-atrial groove tissue, where ganglionic plexi can be located, can be included in tissue to be ablated.

The ablation clamp 310 is shown, in this embodiment, as having one jaw in front (element 325) of the left superior pulmonary vein 315 and the left inferior pulmonary vein 320, and one jaw behind the veins (element 330). The process of ablating the atrial tissue surrounding the pulmonary veins ablation can be continued until sufficient conduction block is achieved, such as with 1 to 4 applications of the clamp, such as two applications or more, or three applications or more, etc. Bidirectional block (e.g., an electrical signal is not transmitted from either direction) can then be confirmed with a sensing device, such as the combination ablation and sensing device disclosed above. In some embodiments, each pulmonary vein can be tested individually for bidirectional block for both pacing and sensing. After bidirectional block is confirmed, the ablation device, such as a clamp, and the guiding catheter or tape can be removed. This completes the ablation, or electrical isolation of tissue around the right set of pulmonary veins, which is shown as element 410 in FIG. 4.

Additional epicardial ablation lines can be made in order to block aberrant conduction through other areas of the heart. A first epicardial ablation line connecting the right inferior pulmonary vein to the left inferior pulmonary vein through the oblique sinus can be made with multiple stamping ablation applications of an ablation device such as the bipolar radiofrequency pen described above. The process of ablation can be continued until sufficient conduction block along the line between the right inferior pulmonary vein and the left inferior pulmonary vein is achieved, such as with 1 to 4 applications of the clamp, such as two applications or more, or three applications or more, etc.

FIG. 4 provides a schematic view of the heart from the posterior aspect, illustrating a map of the ablation lesions created using the methods of the subject invention. The ablation line described above which connects the right inferior pulmonary vein to the left inferior pulmonary vein is shown as element 440 in FIG. 4. Anatomic landmarks include the inferior vena cava (IVC) 401, superior vena cava (SVC) 402, right atrial appendage 403, right atrium 404, right superior pulmonary vein 405, right inferior pulmonary vein 406, left inferior pulmonary vein 407, left superior pulmonary vein 408, left ventricle 409, coronary sinus 411, aorta 412, and left atrial appendage 413.

Figure 2:
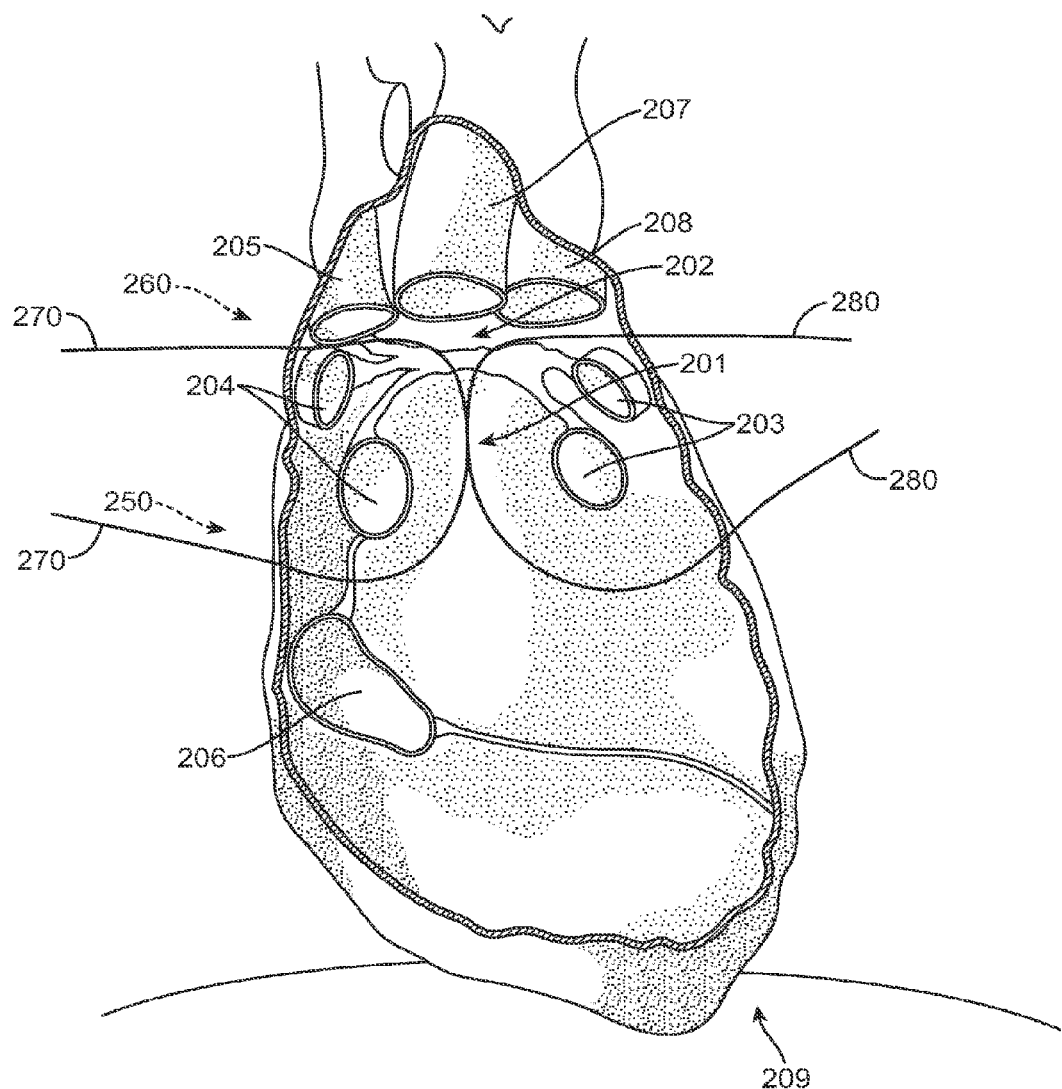
FIG. 2 provides a schematic view of the heart, demonstrating the thoracoscopic access to the epicardial region of the heart according to the methods of the invention.

Although the most common pulmonary vein anatomy is shown in FIG. 2, with two right pulmonary veins 204 and two left pulmonary veins 203, the methods of the subject invention can also be used in patients with anatomic variants. For example, in most patients, the right pulmonary veins include a right superior pulmonary vein and a right inferior pulmonary vein as shown in FIG. 2, however in some patients the right pulmonary veins can also include anatomic variants such as a common trunk of the right pulmonary veins, or a supernumerary vein such as a separate right middle pulmonary vein which drains the right middle lobe of the lung.

In addition to a line connecting the right inferior pulmonary vein to the left inferior pulmonary vein, a second connecting ablation line can be made from the right superior pulmonary vein to left superior pulmonary vein through the transverse sinus posterior to the aorta and the main pulmonary artery in the same manner. An ablation line connecting the right superior pulmonary vein to the left superior pulmonary vein is shown as element 430 in FIG. 4.

A third connecting ablation line which can be produced with the subject methods extends from the superior pulmonary vein connecting ablation line across the dome of the left atrium to the fibrous trigone. The fibrous trigone is an area at the aorto-mitral confluence, at the base of the left coronary and non-coronary commissure of the aortic valve. Exposure to allow creation of this ablation line can be facilitated by using an instrument inserted through the superior port, e.g., a port in the $2^{nd}$ ICS, or $3^{rd}$ ICS, including the $3^{rd}$ ICS medial to the anterior axillary line, which is suitable for retracting tissue (e.g., a soft tissue dissector) which can retract the aorta medially, and the right atrial appendage laterally. A lesion located along this line can be important for preventing atypical atrial flutter and left atrial tachycardia. This third ablation line (shown as element 450 in FIG. 4) forms an interconnecting or T-configuration ablation line with the second ablation line connecting the superior right and left pulmonary veins (element 430).

An additional ablation line can be made from the lesion connecting the right and left inferior pulmonary veins 440 to the coronary sinus, shown as element 480 in FIG. 4. Creation of this ablation line can be facilitated by using an instrument inserted through the most cephalad port (e.g., a port in the 2nd intercostal space, or in the 3rd intercostal space medial to the anterior axillary line) for retraction of the heart anteriorly and retraction of the pericardium laterally. Collateral damage to the circumflex coronary artery can be avoided by direct visualization with the thoracoscope, as well as by creating an ablation line that intersects the coronary sinus sufficiently distal to the coronary sinus ostium, or opening, such that it decreases the risk of damage to the circumflex artery. Verification that the cardiac tissue down to the level of the mitral valve annulus has been reached can be evaluated by transesophageal echocardiography as well as by sensing of atrial and ventricular electrograms, such as with a sensing bipolar pen.

Additional lesions which can be produced from the right thoracoscopic approach include a vertically-oriented ablation line connecting the superior vena cava (SVC) to the inferior vena cava (IVC), which can be made in the same manner as disclosed above, shown as element 500 in FIG. 4. Furthermore, a T-ablation line can be formed which connects the vertical line connecting the SVC to the IVC (element 500) with the lateral aspect of the encircling right pulmonary vein isolation ablation line (element 410), thereby creating a continuous line across the lateral aspect of the atrial septum. This lesion is shown as element 490 in FIG. 4.

In some instances, the methods of the subject invention further include focal ablation of one or more complex fractionated atrial electrograms (CFAEs). CFAEs are areas of cardiac atrial tissue with characteristic morphologically distinct electrograms that may contribute to the initiation and/or propagation of arrhythmias. CFAEs can be located by interrogation from the epicardial surface with a sensing device, such as a sensing pen. One or more complex fractionated atrial electrograms can be ablated from the epicardial approach, using the devices as disclosed above. CFAEs can be sensed and ablated in both left and right atria, as well as in both the superior and inferior vena cavae. The methods can include performing the ablating steps one or more times until it is determined that the CFAE has been ablated (e.g. the characteristic morphology of a complex fractionated atrial electrogram is no longer detected in the region that has been ablated). Further details of techniques of mapping and ablation of CFAEs that can be adapted for use with the subject methods are disclosed in the publication by Nademanee, et al., entitled "A new approach for catheter ablation of atrial fibrillation: mapping of the electrophysiologic substrate". Following the completion of the ablation procedure, a chest tube can be inserted for venting and the right lung re-inflated.

For a left thoracoscopic approach, the operating table can be tilted slightly to the right side with a slight tilt, such as a 15 degree tilt. After the left lung is deflated, one or more openings can be created in the left side of the chest. In one embodiment, four ports can be utilized for performing the methods of the subject invention, as shown in FIG. 1. The first port, shown as element 115 in FIG. 1, can be placed in the $3^{rd}$ or $4^{th}$ intercostal space (ICS) 1 centimeter posterior to the anterior axillary line. A thoracoscope can be introduced and the left hemithorax visually inspected. Humidified $CO_2$ can be introduced into the thoracic cavity at a pressure sufficient to allow adequate visualization for the methods of the invention (e.g., 8 mm Hg pressure). A second port can be placed in the $2^{nd}$ ICS 1 to 2 cm medial to anterior axillary line, shown as element 125 in FIG. 1. The placement of this most cephalad port on the left allows for the exposure for completion of the superior connecting ablation line in the roof of the left atrium. The most cephalad port (e.g., a port in the $2^{nd}$ ICS) can also utilized in the creation or completion of the ablation line from the superior pulmonary vein connecting ablation line across the dome of the left atrium to the fibrous trigone (element 450). A third port can be placed in the $5^{th}$ ICS mid axillary line, shown as element 135 in FIG. 1. The fourth port, element 145 in FIG. 1, can be placed in the $6^{th}$ ICS in the anterior axillary line.

A second thoracoscopic grasping forceps can be introduced through the most caudal port. A second opening can be created in the pericardium on the left side to allow access to the epicardial surface of the heart. In some embodiments, the pericardium can be opened in the most dependent portion posterior to the left phrenic nerve and the opening can be then extended to the level of the diaphragm. The pericardial opening can be enlarged posterior and parallel to the phrenic nerve extending cephalad and superior to the right pulmonary artery. An endograsper or endoKittner can then be introduced through the third port. One or more traction sutures can be placed on the edges of the pericardium, to expose the left atrial appendage in its entirety. As disclosed above, in some embodiments, this is facilitated utilizing an Endo Stitch™ (Autosuture™, Covidien, Mansfield, Mass.), or other similar suture device.

A combination ablation and sensing device as described above can be introduced into the thoracic cavity via the third port. The sensing portion of the device can be used for sense pulmonary vein potentials, to create a baseline map of the left pulmonary vein potentials. Additionally, in some embodiments, autonomic ganglionic plexi can be mapped with high-frequency stimulation and then focally ablated, as disclosed above for the right side.

In some embodiments, the ligament of Marshall and posterior pericardial attachments can be divided, or separated, from the pulmonary artery down to the dome of the left atrium, and then ablated. The ligament of Marshall is a vestigial structure of the vein of Marshall which can also be a source of arrhythmia. Exposure to allow ablation of the ligament of Marshall can be facilitated by using an instrument inserted through the superior port, e.g., a port in the $2^{nd}$ ICS, or $3^{rd}$ ICS, including the $3^{rd}$ ICS medial to the anterior axillary line, which is suitable for retracting tissue (e.g., an endoscopic fan retractor, or a soft tissue dissector such as an endoscopic Kittner) which can retract the left atrial appendage medially and caudally. Simultaneous retraction of the left pulmonary artery cephalad, or in a superior direction, can allow access to the ligament of Marshall. After the ligament of Marshall is divided and ablated, a dissector, such as the Wolf dissector, can be then introduced through the $5^{th}$ ICS port incision (element 135 in FIG. 1) with a guiding element, such as the Glidepath™ Transfer Tape or a red rubber catheter attached. The dissector can be placed into the oblique sinus, and maneuved until the tip passes through the transverse sinus superior and medial to the left superior pulmonary vein. Alternatively, the guiding catheter can be placed from the transverse sinus to the oblique sinus. The Glidepath catheter is grasped and pulled out of the chest, and the dissector disarticulated and removed. The guiding catheter or tape now forms a path between the transverse sinus and the oblique sinus, shown as element 280 in FIG. 2. The distal end of the Glidepath catheter, which has been attached to an ablation device, can then be introduced into the left hemithorax. The guiding element, such as a catheter, can be used to guide one jaw 330 of the clamp 310 in FIG. 2 behind the left pulmonary veins while the other jaw 325 is passed in front of the veins. The process of ablating the atrial tissue surrounding the pulmonary veins ablation can be continued until sufficient conduction block is achieved, such as with 1 to 4 applications of the clamp, including two applications or more, or three applications or more, etc.

In some embodiments, after ablation has been performed, the cardiac tissue can be tested intraoperatively for sufficient conduction block. In some embodiments, each pulmonary vein is tested individually for bidirectional block for both pacing and sensing. After sufficient conduction block is confirmed, the ablation device and the guiding element can be removed. This completes the ablation, or electrical isolation of tissue around the left set of pulmonary veins, which is shown as element 420 in FIG. 4.

The heart can then be retracted anteriorly in order to complete the inferior epicardial ablation line 440 in FIG. 4 by connecting this line to the left pulmonary vein encircling ablation line 420 using a combination ablation and sensing device. The superior epicardial ablation line 430 can be completed by connecting to the left pulmonary vein encircling ablation line 420. An additional ablation line (element 460) can then be made from the base of the left atrial appendage which can be connected to the left pulmonary vein encircling ablation line 420.

In some embodiments, the methods of the subject invention further include amputation of the left atrial appendage (element 470). The left atrial appendage can be a frequent source of thromboemboli in patients with atrial fibrillation. The left atrial appendage can be occluded utilizing an endoscopic no-knife stapling device, such as an Ethicon™ EZ 45 NK device (Ethicon Endo-Surgery, Inc., Cincinnati, Ohio) or a left atrial appendage clip (LAA) clip (AtriCure Inc., Westchester, Ohio) which is placed at the base of the appendage. The line of exclusion for the left atrium is shown as element 470 in FIG. 4. Placement can be confirmed by tranesophageal echocardiography. In embodiments in which staples are used, an initial row of staples can be placed across the base of the left atrial appendage, and if it is determined that the exclusion is incomplete, one or more additional rows of staples can be placed. After the exclusion is complete, the left atrial appendage can be amputated with a cutting stapling device, such as an Ethicon EZ 45 K device, and the appendage removed.

Elements of the Cox maze III set of lesions that can be produced with the methods of the subject invention therefore can include a right pulmonary vein encircling ablation line 410 as shown in FIG. 4, a left pulmonary vein encircling ablation line 420, a superior connecting ablation line connecting the right and left pulmonary vein encircling lines 430, and an inferior connecting ablation line connecting the right and left pulmonary vein encircling lines 440. The combination of ablation lines 410, 420, 430, and 440 comprises what is known as the "box lesion" set. In addition, an ablation line connecting the superior ablation line to the fibrous trigone 450, an ablation line connecting the superior ablation line to the left atrial appendage 460, a left atrial appendectomy 470, and an ablation line extending from the inferior connecting ablation line to the coronary sinus 480 can additionally be produced. In some embodiments, the set of lesions can include an ablation line in the posterior wall of the right atrium connecting the superior vena cava to the inferior vena cava 500, and an ablation line connecting the right pulmonary vein encircling line to an ablation line in the posterior wall of the right atrium connecting the superior vena cava to the inferior vena cava 490. In addition, in some instances the methods can include ablation of autonomic ganglionic plexi. In some embodiments, the methods also include ablation of complex fractionated atrial electrograms, as discussed above.

Although the above ablation lines or lesions have been described in a particular order, the methods of the invention can also include creation of the lesions in any suitable order. For example, the superior epicardial ablation line 430 in FIG. 4 can be completed by connecting to the left pulmonary vein encircling ablation line 420, and then the inferior epicardial ablation line 440 can be completed by connecting this line to the left pulmonary vein encircling ablation line 420.

Furthermore, although the methods of producing ablation lines disclosed above have been described as being performed sequentially, such that the ablation lines are produced first on one side followed by the other side, in some embodiments the methods of the invention can also include the production of ablation lines from both sides simultaneously. The methods of the subject invention can also include the simultaneous use of thoracoscopic instruments from both sides, such as for example, if a thoracoscopic instrument inserted from the left is used to produce an ablation line, and a thoracoscopic instrument inserted from the right is used for retraction, for illumination, etc.

After completion of the ablation procedure as outlined above, the set of lesions that have been created can be tested by attempting to induce an arrhythmia, e.g., atrial fibrillation, by atrial burst pacing. For example, the cardiac tissue can be stimulated at 20 mA for 5 seconds. If an attempt to induce an arrhythmia results in sustained AF, for example, then this can indicate that atrial tissue with the potential of generating or maintaining AF persists. Sustained atrial fibrillation can be defined as AF lasting ≥10 minutes. If an arrhythmia can be induced at the conclusion of the procedure, then additional ablation can be performed. This can include additional ablation, for example, in positive GP sites, or additional ablation in one of the connecting ablation lines, e.g., the connecting ablation line to the left atrial appendage, or ablation of a complex fractionated atrial electrogram, etc.

By this method, an atrial arrhythmia, such as atrial fibrillation, can be successfully treated using a completely thoracoscopic method to produce a set of lesions chosen from among a group of Cox maze III set of lesions as disclosed above. Using the methods of the subject invention, an epicardial Cox maze III ablation procedure can be successfully completed on a beating heart, without the need to place the patient on cardio-pulmonary bypass. In addition, the methods can include thoracoscopically producing a lesion in the ganglionic plexi. Successful ablation can be verified with intraoperative electrophysiologic testing.

The subject methods find use in treating a cardiac arrhythmia, such as atrial fibrillation, by the epicardial ablation of cardiac tissue through openings in a subject's body using thoracoscopic methods. Although the Cox maze III set of lesions can be used for the treatment of AF, the methods of the subject invention can also be used to treat multiple cardiac arrhythmias, including but not limited to: all types of atrial fibrillation, including paroxysmal, persistent, long-standing persistent, and permanent AF, atrial flutter; atrioventricular (AV) node reentrant tachycardias; and atrioventricular (AV) reentry tachycardia (such as Wolff-Parkinson-White syndrome), and therefore any appropriate cardiac arrhythmia may be treated as described herein. Furthermore, the methods of the subject invention may also be used in combination with other thoracoscopic procedures. Although the methods as described above are directed to creation of a Cox maze III set of lesions in the atria, the methods of thoracoscopically producing a set of lesions can also be used to treat ventricular arrhythmias.

The subject methods also include the step of diagnosing a patient in need of surgical treatment for a cardiac arrhythmia, e.g., atrial fibrillation. Patients who need surgical treatment for an arrhythmia can include, for example, patients who cannot be anticoagulated, or patients who have failed medical therapy, or who cannot tolerate the side effects of anti-arrhythmic drugs.

Cardiac arrhythmias can have many different causes. For example, atrial fibrillation can have both cardiovascular causes (such as hypertensive heart disease, coronary artery disease, valvular heart disease, cardiomyopathies) and non-cardiovascular causes (such as lung disease, obesity, sleep apnea, metabolic disorders, toxins).

Therefore, the signs and symptoms associated with a cardiac arrhythmia will vary depending on the arrhythmia, and upon any associated condition. Signs and symptoms can include abnormal awareness of the heartbeat, or palpitations, lightheadedness or dizziness, shortness of breath, decreased exercise tolerance, fatigue, fainting. Some arrhythmias can result in cardiac failure, cardiac arrest, or sudden death. Some forms of arrhythmia may not cause symptoms, but can increase the risk of stroke. For example, patients with atrial fibrillation have an increased risk of embolism, transient ischemic attacks (TIAs), and stroke. Cardiac arrhythmias are often first detected by an abnormal peripheral pulse, or by auscultation of the heart with a stethoscope. These methods may not be sufficient to diagnose specific arrhythmias, but can give a general indication of the heart rate and whether it is regular or irregular.

Diagnostic tests can include physical examination, electrocardiogram (EKG; ECG); a Holter monitor, which is an EKG recorded over a 24-hour period to detect arrhythmias that may happen briefly and unpredictably throughout the day, imaging studies such as chest x-ray, ultrasound, computerized tomography (CT), magnetic resonance imaging (MRI), nuclear medicine studies such as a nuclear myocardial stress test, for example. Additionally, invasive studies including cardiac catheterization with electrophysiologic studies may be performed.

Treatment for arrhythmias, including AF, can include anti-arrhythmic drugs to prevent or control arrhythmias, and maintain the normal sinus rhythm of the heart. Medication to prevent clotting is also indicated in patients who are at risk for clots and emboli, which are clots which travel elsewhere in the body and can cause strokes, for example. Invasive treatments can include catheter ablation or modification of the atrioventricular (AV) node, with concomitant pacing of the heart, and catheter or surgical ablation procedures, such as the Cox maze III procedure.

The description of the present invention is provided herein in certain instances with reference to a subject or patient. As used herein, the terms "subject" and "patient" refer to a living entity such as an animal. In certain embodiments, the animals are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In certain embodiments, the subjects, e.g., patients, are humans.

The following example is offered by way of illustration and not by way of limitation.

Experimental

A patient with a diagnosis of atrial fibrillation was prepared for a thoracoscopic epicardial ablation procedure in a conventional manner. The patient was placed supine on the operating table with both arms at his side and slightly flexed at the elbows. A roll was placed transversely across and underneath the tips of the scapulae. General anesthesia was administered with a double-lumen endotracheal tube for single lung ventilation. A right internal jugular venous introducer sheath was inserted for central venous pressure monitoring as well as for intravenous fluid administration. Transesophageal echocardiography monitoring was performed during the entire procedure.

Right Thoracoscopic Approach

The table was tilted slightly to the left side with a 15 degree tilt. The right lung was deflated. Four ports were utilized. The first 12 mm port was placed in the $4^{th}$ intercostal space (ICS) 1 centimeter posterior to the anterior axillary line. The thoracoscope was then introduced and the right hemithorax visually inspected. Humidified $CO_2$ insufflation (8 mm Hg pressure) was instituted and maintained throughout the procedure. The second 12 mm port was placed in the $3^{rd}$ ICS 1 cm medial to anterior axillary line. A 5 mm port was placed in the $5^{th}$ ICS mid-axillary line. The third 12 mm port was placed in the $6^{th}$ ICS in the anterior axillary line, for a total of four ports. The pericardium was opened cephalad to the confluence of the right atrial appendage and ascending aorta. The opening was extended cephalad, or superiorly, to the level of the aorta, 2 cm anterior and parallel to the right phrenic nerve, and was extended inferiorly to the level of the inferior vena cava (IVC). Two traction sutures were placed and exteriorized. This was facilitated utilizing an Endo Stitch™×2 (Autosuture™, Covidien, Mansfield, Mass.). The oblique sinus was opened bluntly with endoKittner. The transverse sinus was entered with retraction of the SVC anteriorly with endoKittner and entry into the transverse sinus was confirmed with visualization of the left atrial appendage. The Wolf™ Lumitip™ dissector (Atricure, Inc., Cincinnati, Ohio) was introduced through the oblique sinus and then articulated with the tip exiting in the transverse sinus posterior to the right set of pulmonary veins. The posterior space between the pericardium and left atrium was then enlarged with blunt dissection. The dissector was then removed.

Atrial electrograms and pulmonary vein potentials were then sensed to record a baseline. Autonomic ganglionic plexi were mapped with high-frequency stimulation and then active GPs, defined as those resulting in a lengthening of the R-R interval of greater than 50%, were focally ablated. The Lumitip dissector was then introduced through the anterior/cephalad port incision (port site #2) with the Glidepath™ Transfer Tape (Atricure, Inc., Cincinnati, Ohio) catheter attached. This was placed through the transverse sinus with the tip posterior to the right set of pulmonary veins. The dissector was then articulated with the tip exiting through the oblique sinus between the right inferior pulmonary vein and IVC. The Glidepath catheter was grasped and exteriorized and the dissector disarticulated and removed. The distal end of the Glidepath catheter was attached to the bipolar radiofrequency (RF) Isolator® Synergy™ Cardiac Ablation Clamp (Atricure, Inc., Cincinnati, Ohio) and then was introduced into the right hemithorax and the catheter was used to guide the lower jaw of the clamp behind the right pulmonary veins while the upper jaw was passed in front of the veins. Five applications of the clamp were sufficient to provide conduction block. The patient was defibrillated into sinus rhythm and bidirectional block was confirmed with the bipolar pace/sense/stimulation pen. After bidirectional block was confirmed, the clamp and catheter were removed.

Epicardial ablation lines were then made connecting the right inferior pulmonary vein to the left inferior pulmonary vein through the oblique sinus with multiple stamping ablation applications of the bipolar ablation pen. A second connecting ablation line was made from right superior pulmonary vein to left superior pulmonary vein through the transverse sinus posterior to the aorta and main pulmonary artery in the same manner. Then a connecting ablation line from the fibrous trigone under the aorta was made as an interconnecting or T-ablation line to the superior vein connecting ablation line. An ablation line connecting the superior vena cava to the inferior vena cava was then made and finally a T-ablation line from this line to the encircling right pulmonary vein isolation ablation line was made, thereby ablating the lateral aspect of the atrial septum. Complex fractionated atrial electrograms were mapped and focally ablated at the base of the right atrial appendage as well as the lateral free wall of the right atrium. A 24 Fr chest tube was inserted for venting and the right lung inflated.

Left Thoracoscopic Approach

The table was tilted toward the right 15 degrees and the left lung was deflated. Four ports were utilized. The first 12 mm port was placed in the $4^{th}$ intercostal space (ICS) 1 centimeter posterior to the anterior axillary line. The endoscope was then introduced and the left hemithorax visually inspected. Humidified $CO_2$ insufflation (8 mm Hg pressure) was instituted and maintained throughout the procedure. The second 12 mm port was placed in the $2^{nd}$ ICS 2 cm medial to anterior axillary line. A third 5 mm port was placed in the $6^{th}$ ICS mid axillary line. The third 12 mm port was placed 1 cm posterior to the mid-axillary line in the $5^{th}$ ICS. The pericardium was opened in the most dependent portion posterior to the left phrenic nerve and extended to the level of the diaphragm. The opening was then enlarged posterior and parallel to the phrenic nerve extending cephalad and superior to the right pulmonary artery. A traction suture was placed anteriorly to expose the left atrial appendage in its entirety and exteriorized through a stab incision in the 2nd ICS in the mid-clavicular line.

With the patient in sinus rhythm, pulmonary vein potentials were then sensed as well as paced. Autonomic ganglionic plexi were mapped with high-frequency stimulation and then focally ablated. The ligament of Marshall and posterior pericardial attachments were divided from the dome of the left atrium. The Lumitip dissector was then introduced through the $5^{th}$ ICS port incision with the Glidepath catheter attached. The dissector was then articulated with the tip exiting superior and medial to the left superior pulmonary vein. The Glidepath catheter was grasped and exteriorized and the dissector disarticulated and removed. The distal end of the Glidepath catheter was already attached to the bipolar radiofrequency (RF) Isolator® Synergy™ Cardiac Ablation Clamp (Atricure, Inc., Cincinnati, Ohio) which was then introduced into the left hemithorax. The catheter was used to guide the lower jaw of the clamp behind the left pulmonary veins while the upper jaw was passed in front of the veins. Six applications of the clamp were sufficient to provide conduction block. Bidirectional block was then confirmed with the bipolar pace/sense/stimulation pen. After bidirectional block was confirmed, the clamp and catheter were removed.

The heart was then retracted anteriorly and then the inferior epicardial ablation line was completed by connecting to the left pulmonary vein encircling ablation line. The superior epicardial ablation line was completed by connecting to the left pulmonary vein encircling ablation line. An ablation line was then made from the mid portion of the left atrial appendage down to its base and then connected to the left pulmonary vein encircling ablation line. A connecting ablation line to the coronary sinus from the inferior connecting ablation line was then performed. The Cox maze III lesion set was then completed.

Amputation of the Left Atrial Appendage

The left atrial appendage was occluded utilizing an endoscopic no-knife stapling device (Ethicon EZ 45 NK) which was placed at the base of the appendage and confirmed by tranesophageal echocardiography. This allowed for safe occlusion. Finally, the left atrial appendage was amputated with a cutting stapling device (Ethicon EZ 45 K). The appendage was then removed.

Confirmation of Non-Inducibility

Non-inducibility of AF was assessed by atrial burst pacing at a 200 msec cycle length for 5 seconds. Sustained AF was defined as AF lasting $>/=30$ seconds.

At the conclusion of the procedure, the subject was in normal sinus rhythm. The chest and skin incisions were then closed to complete the procedure. The procedure took 3 hours and 20 minutes to complete. Follow-up evaluation of the patient by 21 day mobile cardiac outpatient telemetry at 6 months and 1 year demonstrated documented maintenance of sinus rhythm without anti-arrhythmic medication.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of treating a subject for a cardiac arrhythmia, the method comprising producing a Cox maze III set of lesions in a manner sufficient to treat the subject for the cardiac arrhythmia, wherein the set of lesions comprises a lesion in a ganglionic plexus.

2. The method according to claim 1, wherein the set of lesions is produced by contacting cardiac tissue with an ablation device.

3. The method according to claim 2, wherein the ablation device is a clamping device.

4. The method according to claim 2, wherein the ablation device is a radiofrequency device.

5. The method according to claim 2, wherein the ablation device is a laser energy device.

6. The method according to claim 2, wherein the ablation device is a microwave energy device.

7. The method according to claim 2, wherein the ablation device is a thermal energy device.

8. The method according to claim 2, wherein the ablation device is an ultrasound device.

9. The method according to claim 2, wherein the ablation device is a cryoablation device.

10. The method according to claim 1, wherein the cardiac arrhythmia comprises atrial fibrillation.

11. A method of treating a subject for a cardiac arrhythmia, the method comprising producing a set of lesions comprising a right pulmonary vein encircling ablation line, a left pulmonary vein encircling ablation line, a superior connecting ablation line connecting the right and left pulmonary vein encircling lines, an inferior connecting ablation line connecting the right and left pulmonary vein encircling lines and an ablation line connecting the superior connecting ablation line to the base of the left atrial appendage.

12. The method according to claim 11, wherein the set of lesions further comprises a left atrial appendectomy.

13. The method according to claim 11, wherein the set of lesions further comprises an ablation line connecting the superior connecting ablation line to the fibrous trigone.

14. The method according to claim 11, wherein the set of lesions further comprises an ablation line extending from the inferior connecting ablation line to the coronary sinus.

15. The method according to claim 11, wherein the set of lesions further comprises an ablation line in the posterolateral wall of the right atrium connecting the superior vena cava to the inferior vena cava.

16. The method according to claim 11, wherein the set of lesions further comprises an ablation line from the right pulmonary vein encircling ablation line to the posterolateral wall of the right atrium.

17. The method according to claim 11, wherein the set of lesions further comprises focal ablation of a complex fractionated atrial electrogram.

18. The method according to claim 11, wherein the lesions are produced with an ablation device.

19. The method according to claim 18, wherein the ablation device is a radiofrequency device.

20. The method according to claim 11, wherein the cardiac arrhythmia comprises atrial fibrillation.

* * * * *